United States Patent
Arai

(10) Patent No.: US 11,110,596 B2
(45) Date of Patent: Sep. 7, 2021

(54) MASTER-SLAVE MANIPULATOR AND CONTROL METHOD THEREFOR

(71) Applicant: OLYMPUS CORPORATION, Tokyo (JP)

(72) Inventor: Takeshi Arai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 160 days.

(21) Appl. No.: 16/684,845

(22) Filed: Nov. 15, 2019

(65) Prior Publication Data

US 2020/0078933 A1 Mar. 12, 2020

Related U.S. Application Data

(63) Continuation of application No. PCT/JP2018/019730, filed on May 26, 2017.

(51) Int. Cl.
  *B25J 9/00* (2006.01)
  *B25J 9/16* (2006.01)
  *B25J 3/00* (2006.01)

(52) U.S. Cl.
  CPC .............. *B25J 9/0081* (2013.01); *B25J 3/00* (2013.01); *B25J 9/1689* (2013.01)

(58) Field of Classification Search
  CPC .................. B25J 9/00; B25J 9/16; B25J 3/00
  See application file for complete search history.

(56) References Cited

U.S. PATENT DOCUMENTS

| | | | | |
|---|---|---|---|---|
| 2012/0059519 A1* | 3/2012 | Kishi | .................... | A61B 34/74 700/264 |
| 2012/0143353 A1* | 6/2012 | Kishi | .................... | A61B 34/30 700/3 |
| 2014/0005708 A1* | 1/2014 | Shelton, IV | ........... | A61B 17/29 606/170 |
| 2014/0052155 A1* | 2/2014 | Hourtash | ............... | A61B 34/37 606/130 |

(Continued)

FOREIGN PATENT DOCUMENTS

| | | |
|---|---|---|
| EP | 2594372 A1 | 5/2013 |
| EP | 2617530 A1 | 7/2013 |

(Continued)

OTHER PUBLICATIONS

International Search Report dated Aug. 22, 2017 issued in PCT/JP2017/019730.

*Primary Examiner* — Kira Nguyen

(74) *Attorney, Agent, or Firm* — Scully, Scott, Murphy & Presser, P.C.

(57) ABSTRACT

A master-slave manipulator according to the present invention includes a remote operation device, serving as a master, that provides operation information corresponding to multiple degrees of freedom, a slave manipulator having a plurality of joints corresponding to multiple degrees of freedom and including a redundant joints among the joints, and a controller that controls the operation of the joints in accordance with the operation information, in which, when it is determined that a distal end of the slave manipulator operates, the controller determines, among the redundant joints, drive ratios α of a joint disposed on a base end side and a joint disposed on a distal end side within a range of 0<α<1, respectively, and drives the joints.

14 Claims, 9 Drawing Sheets

(56) References Cited

U.S. PATENT DOCUMENTS

| | | |
|---|---|---|
| 2014/0277741 A1 | 9/2014 | Kwon et al. |
| 2015/0321355 A1 | 11/2015 | Kishi |
| 2016/0135909 A1* | 5/2016 | Ogawa .................. A61B 34/37 606/130 |
| 2017/0120457 A1* | 5/2017 | Saraliev ............... A61B 90/361 |
| 2017/0273748 A1* | 9/2017 | Hourtash .............. A61B 34/74 |
| 2018/0353251 A1* | 12/2018 | Cuthbertson .......... A61B 34/71 |

FOREIGN PATENT DOCUMENTS

| | | |
|---|---|---|
| EP | 2777597 A2 | 9/2014 |
| JP | S63-267177 A | 11/1988 |
| JP | 2012-055996 A | 3/2012 |
| JP | 2012-131014 A | 7/2012 |
| JP | 2014-180751 A | 9/2014 |
| JP | 2015-534835 A | 12/2015 |
| WO | WO 2014/084408 A1 | 6/2014 |

* cited by examiner

MASTER-SLAVE MANIPULATOR AND CONTROL METHOD THEREFOR

CROSS-REFERENCE TO RELATED APPLICATIONS

This is a continuation of International Application PCT/JP2017/019730, with an international filing date of May 26, 2017, which is hereby incorporated by reference herein in its entirety.

TECHNICAL FIELD

The present invention relates to a master-slave manipulator and a control method therefor.

BACKGROUND ART

There is a known master-slave manipulator in which a redundant roll axis joint is provided at a distal end of a slave arm that is to be inserted into a body cavity, thereby making it possible to determine the position and orientation of only the distal end within a narrow body cavity (for example, see Japanese Unexamined Patent Application, Publication No. Sho 63-267177).

SUMMARY OF INVENTION

According to an aspect of the present invention, a master-slave manipulator includes a remote operation device as a master that provides operation information corresponding to multiple degrees of freedom, a slave manipulator having a plurality of joints corresponding to multiple degrees of freedom and including a redundant joints among the joints, and a controller that controls the operation of the joints in accordance with the operation information, in which the controller, depending on whether or not work is being performed by the slave manipulator, determines the drive ratios α (0<α<1) of the joints in a redundant relationship and drives these joints.

DESCRIPTION OF EMBODIMENTS

A master-slave manipulator 1 according to an embodiment of the present invention will be described below with reference to the drawings.

Figure 1:
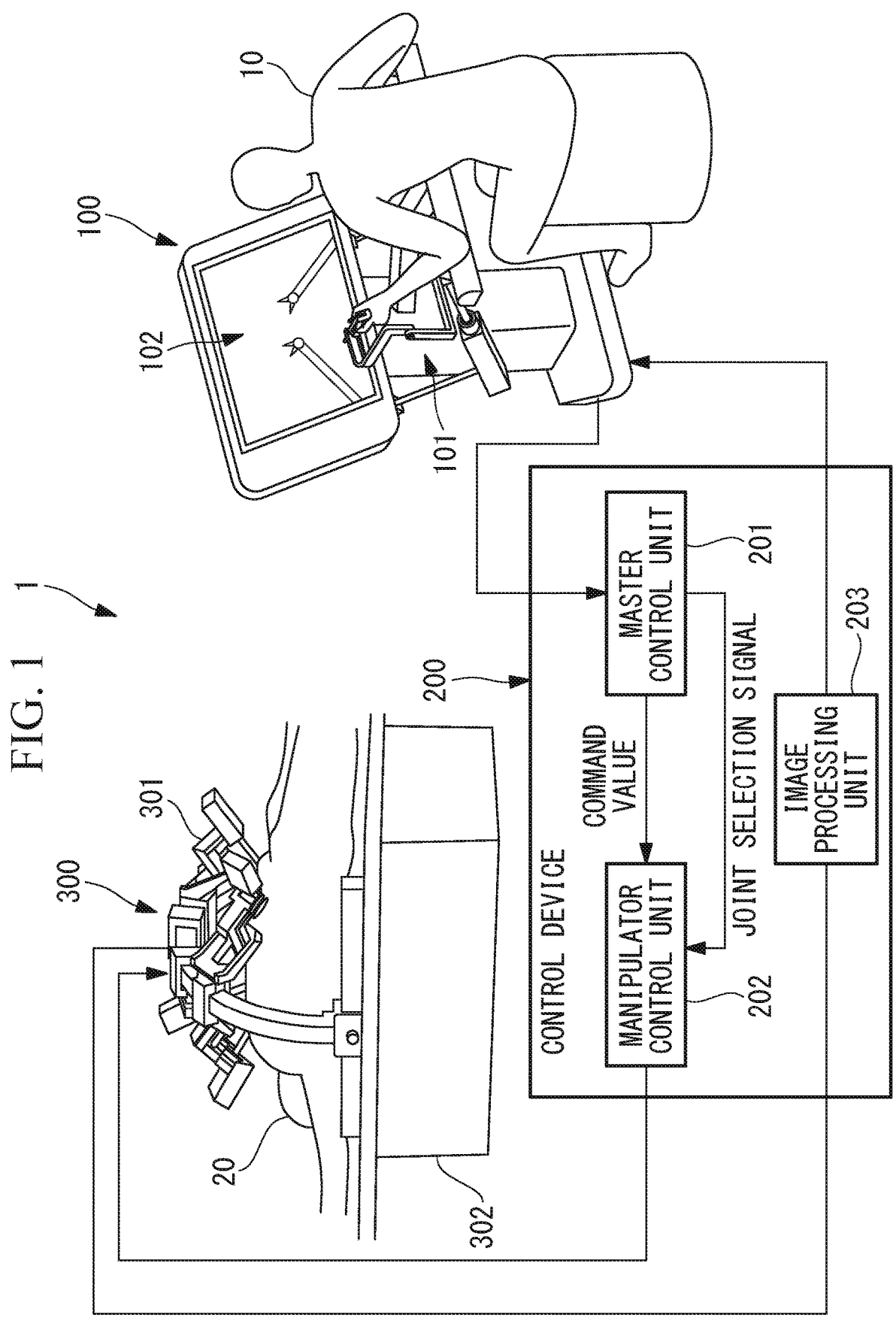
FIG. 1 is an overall configuration diagram illustrating a master-slave manipulator according to an embodiment of the present invention.

The master-slave manipulator 1 according to the present embodiment includes, as illustrated in FIG. 1, a remote operation device 100 operated by an operator 10, a control device 200, and a slave manipulator 300. The example in FIG. 1 is an application example of the master-slave manipulator 1 of the present embodiment for medical use. However, the master-slave manipulator 1 of the present embodiment is applicable to various uses other than medical use.

The remote operation device 100 functions as a master in the master-slave manipulator 1 and includes an operation unit (input unit) 101 and a display unit 102.

Figure 2:
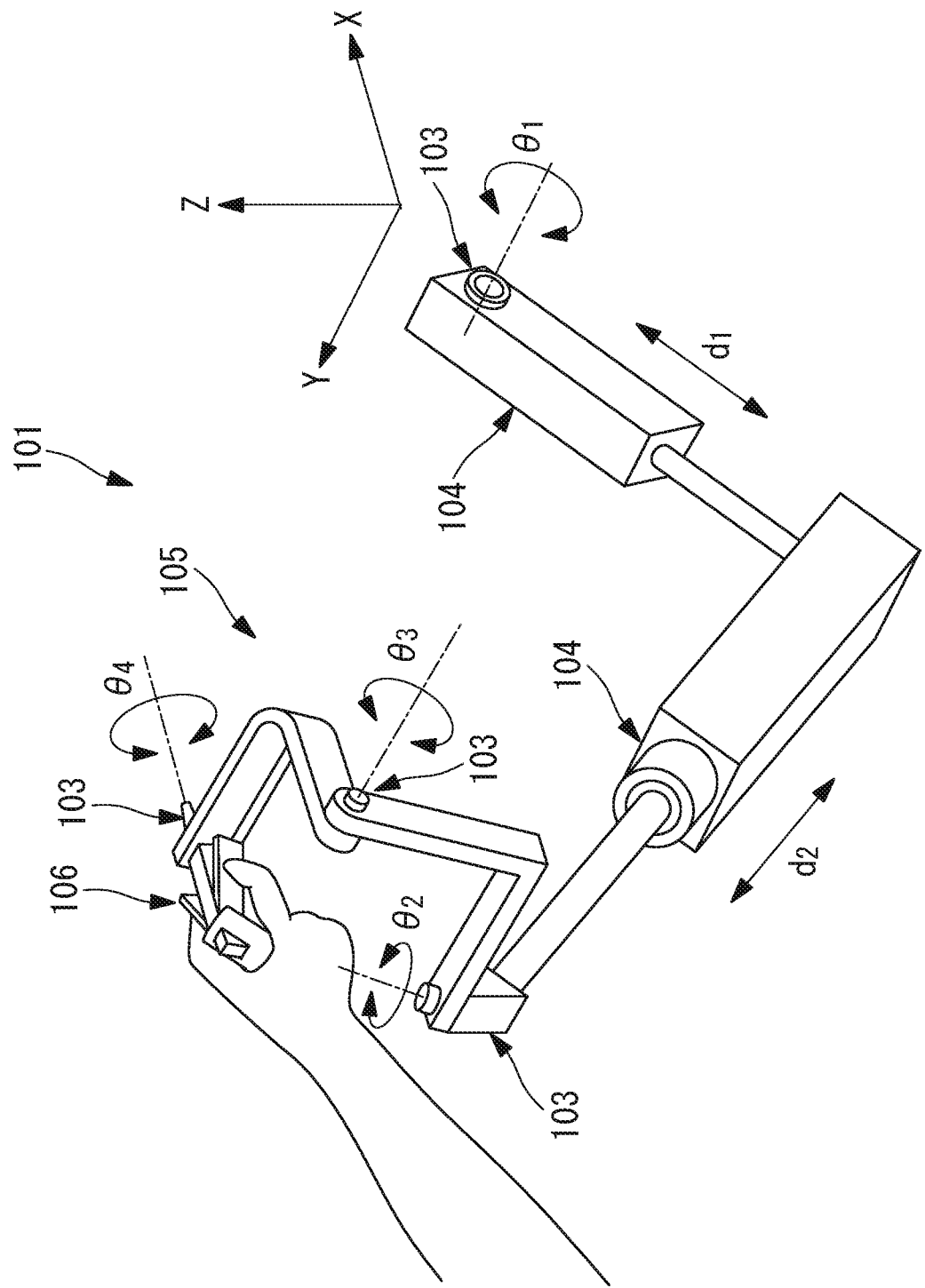
FIG. 2 is a diagram illustrating a configuration example of a remote operation device of the master slave manipulator in FIG. 1.

For example, as illustrated in FIG. 2, the operation unit 101 has a drive unit 105 including drive shafts 103 each formed of a rotation mechanism and drive shafts 104 each formed of a linear motion mechanism. Furthermore, a gripper unit 106 is provided at a terminal end portion of the operation unit 101 (the side gripped by the operator 10).

In such a configuration, the operator 10, while holding the gripper unit 106, moves or rotates the operation unit 101 or operates the gripper unit 106 thereby driving the drive shafts 103 and 104 forming the operation unit 101. The drive amount of each of the drive shafts 103 and 104 (rotation angle in the case of a rotation mechanism, displacement amount in the case of a linear motion mechanism) is detected by a position detector (for example, an encoder) (not illustrated) provided on each of the drive shafts 103 and 104.

The detection signal of each position detector is output to the control device 200 as a signal (operation signal) indicating operation information of the operation unit 101 for sending a command for positioning and orienting a hand (fingers) of a slave arm 301 of the slave manipulator 300. Here, in FIG. 2, the operation unit 101 is provided with six drive shafts 103 and 104, and operation signals (signals related to position ($\theta1$, $d1$, $d2$) and signals related to orientation ($\theta2$, $\theta3$, $\theta4$)) corresponding to six degrees of freedom for calculating six command values are output by driving these six drive shafts 103 and 104.

The configuration of the operation unit 101 is not particularly limited as long as the operation unit 101 can send a command for positioning and orienting the hand (fingers) of the slave arm 301. For example, if the operation unit 101 is provided with a sensor for detecting translation along three horizontal axes (for example, an acceleration sensor) and a sensor for detecting rotation around each drive shaft 103 (for example, an angular velocity sensor), for example, the operation unit 101 can be configured as a hand-held operation unit as illustrated in FIG. 3.

Figure 3:
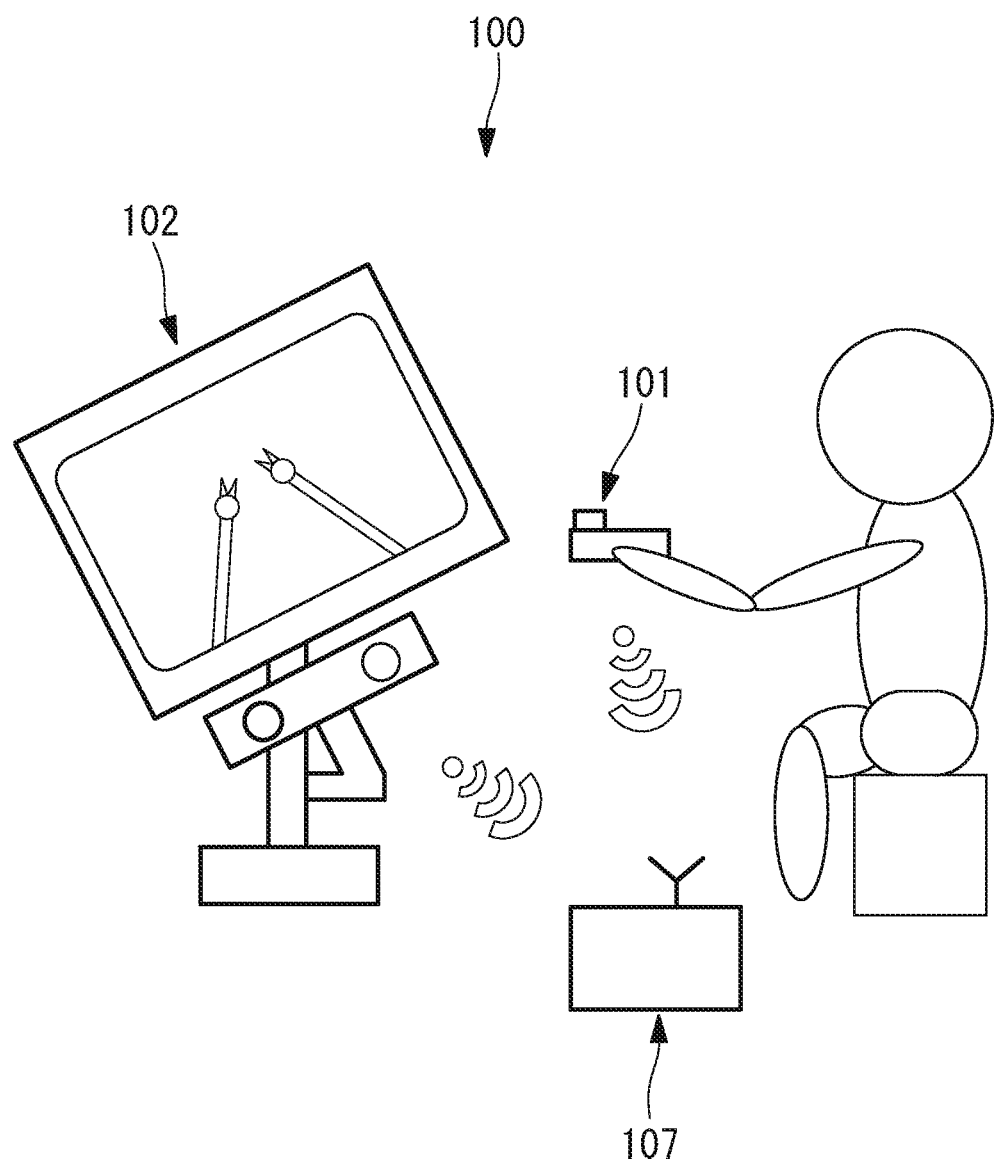
FIG. 3 is a view illustrating a modification of the remote operation device in FIG. 2.

In the example in FIG. 3, the operator 10 can provide operation signals corresponding to six degrees of freedom by moving or rotating the hand-held operation unit 101 in a three-dimensional space. FIG. 3 illustrates an example in which the operation signals obtained by the operation unit 101 can be wirelessly communicated via a wireless communication unit 107. Of course, in the example in FIG. 3, the operation signals obtained by the operation unit 101 may be communicated by wire.

The display unit 102 is, for example, formed of a liquid crystal display and displays an image based on an image signal input from the control device 200. As will be described later, the image signal input from the control device 200 is obtained by processing, in the control device 200, an image signal obtained through an electronic camera (electronic endoscope) attached to the slave arm 301. By displaying an image based on such an image signal on the display unit 102, it is possible for the operator 10 of the remote operation device 100 to check the image of the hand (fingers) of the slave manipulator 300 arranged at a location away from the remote operation device 100.

The control device 200, serving as a controller, includes a master controller 201, a manipulator controller 202, and an image processing unit 203.

The master controller 201 calculates command values for the position and orientation of the hand (fingers) of the slave arm 301 in accordance with operation signals corresponding to six degrees of freedom from the remote operation device 100. The master controller 201 calculates drive ratios α (0<α<1) of joints in a redundant relationship among the individual joints of the slave arm 301 (redundant joints) in accordance with the operation signals from the remote operation device 100, and outputs the calculated drive ratios α to the manipulator controller 202 together with the position and orientation command values.

The manipulator controller 202 receives the command values of the position and orientation from the remote operation device 100 and the drive ratios α of the redundant joints, and calculates, by inverse kinematic calculations, the drive amounts of the respective joints of the slave arm 301 that are necessary to match the position and orientation of the hand (fingers) of the slave arm 301 with the command values.

As will be described later, the slave arm 301 of the present embodiment has joints corresponding to seven degrees of freedom; however, driving is performed by determining the drive ratios α of two redundant joints, and thus, even if the structure is different from the remote operation device 100, redundant degrees of freedom can be selectively controlled to perform intuitive operations including redundant degrees of freedom.

The image processing unit 203 processes an image signal obtained from an electronic camera (such as an electronic endoscope) provided at the distal end of the slave arm 301, generates an image signal for display on the display unit 102, and outputs the image signal to the display unit 102.

The slave manipulator 300 includes the slave arm 301 and an operating table 302.

Figure 4:
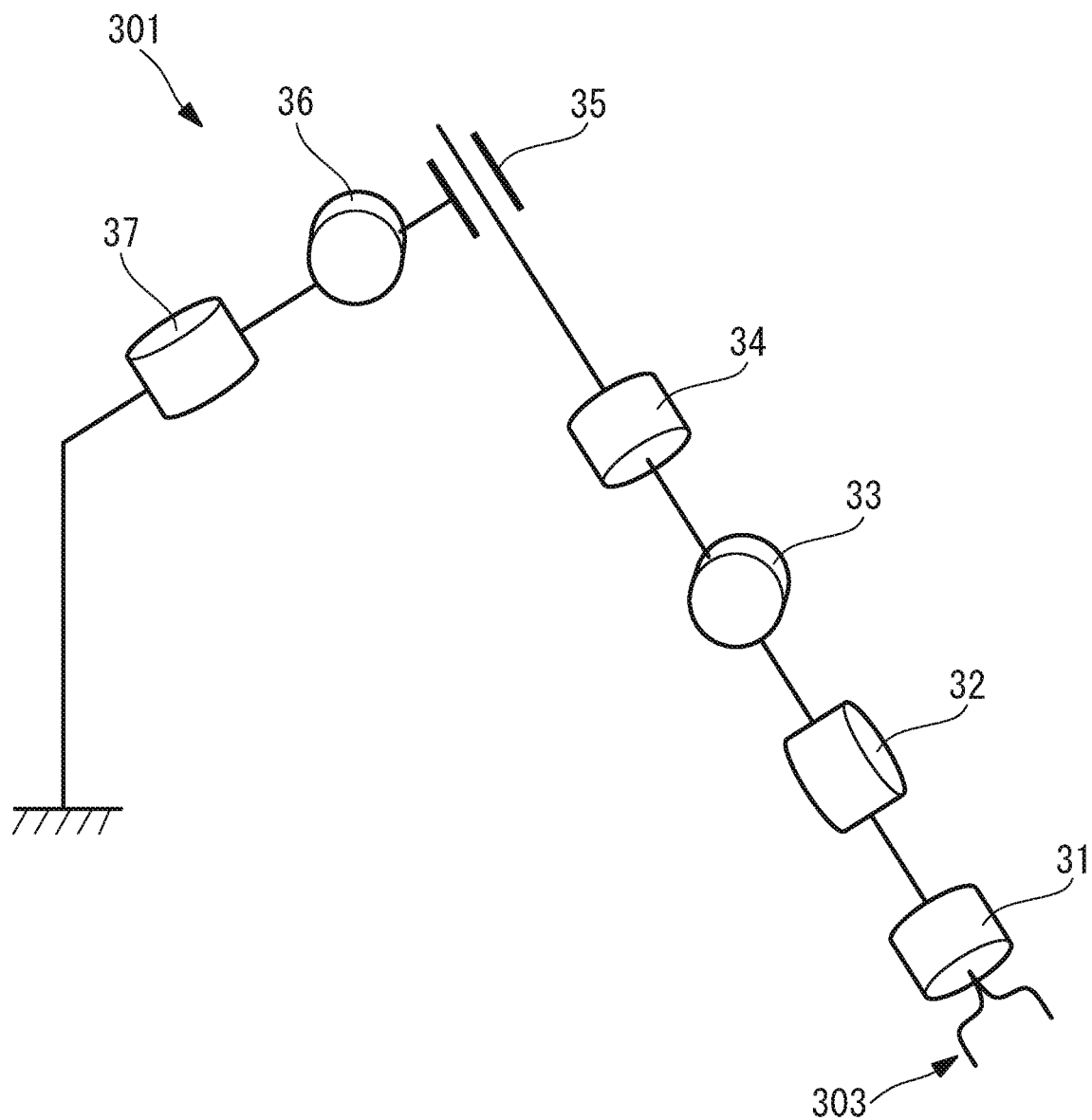
FIG. 4 is a diagram illustrating a configuration example of a slave manipulator of the master-slave manipulator in FIG. 1.

The slave arm 301 has joints corresponding to seven degrees of freedom, and each joint is driven in accordance with a control signal from the manipulator controller 202. As illustrated in FIG. 4, the slave arm 301 has seven joints 31, 32, 33, 34, 35, 36, and 37 arranged in series, and an end effector 303 is attached to a distal end portion. The end effector 303 illustrated in FIG. 4 is an example of a gripper. In addition, a camera (electronic endoscope) or the like may be attached to the distal end portion.

Among the joints 31, 32, 33, 34, 35, 36, and 37 illustrated in FIG. 4, the joints 31 and 34 are joints that rotate about a roll axis (corresponding to the X axis of the master illustrated in FIG. 2), the joints 32 and 37 are joints that rotate about a yaw axis (corresponding to the Z axis of the master illustrated in FIG. 2), and the joints 33 and 36 are joints that rotate about a pitch axis (corresponding to the Y axis of the master illustrated in FIG. 2). The joint 35 is a joint that extends and contracts along the roll axis. Here, in the example in FIG. 4, all seven joints 31, 32, 33, 34, 35, 36, and 37 are independent. In particular, FIG. 4 illustrates an example in which the adjacent joints 31, 32, 33, 34, 35, 36, and 37 operate in accordance with the different drive shafts 103 and 104.

As illustrated in FIG. 4, by driving the joints 32, 33, 34, 35, 36, and 37 other than the joint 31 in cooperation with each other, three degrees of freedom of the position and three degrees of freedom of the orientation of the hand (fingers) on the slave arm 301 are realized. In addition to the joints 32, 33, 34, 35, 36, and 37, in FIG. 4, the joint 31 for rolling the end effector 303 is provided as a redundant joint.

With such a configuration, for example, when the slave arm 301 is caused to roll, it is possible to determine drive ratios α at appropriate times as to whether the joint 34 that is far from the distal end side is to be rolled by a large amount or the joint 31 that is close to the distal end side is to be rolled by a large amount. In the present embodiment, the joint 31 and the joint 34 are driven simultaneously in accordance with the calculated drive ratios α.

The operating table 302 is a table on which a patient 20 is placed and, for example, the slave arm 301 is installed on the operating table 302.

Hereinafter, the operation of the master-slave manipulator 1 of the present embodiment will be described.

The operator 10 holding the gripper unit 106 of the remote operation device 100 moves or rotates the operation unit 101 while holding the gripper unit 106 provided in the operation unit 101 of the remote operation device 100, and, by operating the gripper unit 106, the drive shafts 103 and 104 constituting the operation unit 101 are driven. When the drive shafts 103 and 104 are driven, drive amounts are detected by position detectors (not illustrated), and a detection signal (operation signal) of each of the position detectors is output to the control device 200. Operation signals are output every predetermined time Δt.

The master controller 201 of the control device 200 calculates command values for the position and orientation of the hand (fingers) of the slave arm 301 in accordance with operation signals corresponding to six degrees of freedom from the remote operation device 100. The master controller 201, in accordance with the operation signals from the remote operation device 100, determines the drive ratios α of the joints 31 and 34 in a redundant relationship among the joints 31, 32, 33, 34, 35, 36, and 37 of the slave arm 301, and outputs these drive ratios α to the manipulator controller 202 together with the position and orientation command values.

Here, an example of a method for determining the drive ratio α will be described.

As illustrated in FIG. 4, the slave arm 301 of the example of the present embodiment has, in addition to the joints 32, 33, 34, 35, 36, and 37 corresponding to six degrees of freedom, one roll shaft joint 31 that can be driven independently of the other joints 32, 33, 34, 35, 36, and 37 as a redundant joint, and performs driving corresponding to seven degrees of freedom. When performing inverse kinematics calculations for determining the drive amount of each of the joints 31, 32, 33, 34, 35, 36, and 37 of the slave arm 301 from the position and orientation command values of the hand (fingers) of the slave arm 301, when the number of command values matches the number of drive joints of the slave arm 301, the drive amount of each of the joints 31, 32, 33, 34, 35, 36, and 37 can be uniquely determined by inverse kinematic calculations, and the calculations are not so complicated.

On the other hand, when the number of drive joints of the slave arm 301 is larger than the number of command values of the remote operation device 100, the calculations become complicated. In the present embodiment, a weight matrix is generated by determining the drive ratios α of the joint 31 (referred to as Roll 2) that is a redundant joint and the joint 34 (referred to as Roll 1) that is in a redundant relationship with the joint 31, and inverse kinematics calculations are performed using the weight matrix. As a result, in the inverse kinematics calculations, it is possible to limit the degrees of freedom of the two redundant joints 31 and 34, and the slave arm 301 having 7 degrees of freedom can be considered as the slave arm 301 having substantially 6 degrees of freedom, and intuitive operation including redundant degrees of freedom can be performed.

How to determine the drive ratios α of Roll 1 and Roll 2 is determined by the orientation change amount and the position change amount of the remote operation device 100 every predetermined time. This concept will be described below.

First, the orientation change amount and the position change amount of the remote operation device 100 are defined as follows. For example, it is assumed that the position of the operation unit 101 of the remote operation device 100 at a certain time t is a position Om(t) illustrated in FIG. 5. The orientation of the operation unit 101 at time t is such that the master roll axis Xm, the master pitch axis Ym, and the master yaw axis Zm are respectively in the directions of Xm(t), Ym(t), and Zm(t) illustrated in FIG. 5. From this state, it is assumed that the position of the operation unit 101 has changed to a position Om(t+1) illustrated in FIG. 5 at time t+1 after a predetermined time Δt has elapsed. The position change amount of the operation unit 101 at this time is Om(t+1)−Om(t).

Figure 5:
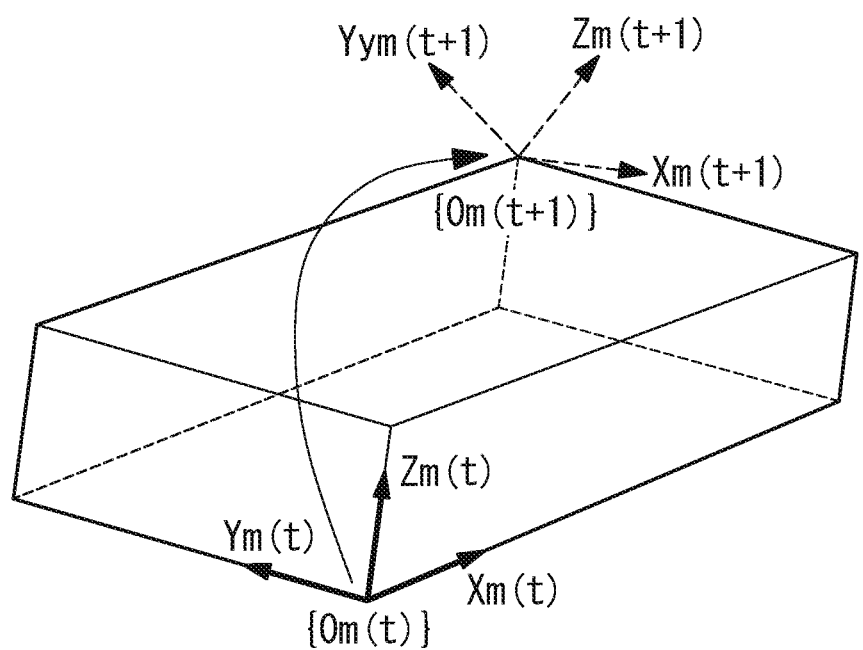
FIG. 5 is a diagram for explaining a position change amount and an orientation change amount of an operation unit of the master-slave manipulator in FIG. 1.

The orientation of the operation unit 101 at time t+1 is changed such that the master roll axis Xm, the master pitch axis Ym, and the master yaw axis Zm are in the directions Xm(t+1), Ym(t+1), and Zm(t+1) illustrated in FIG. 5. At this time, the component of the orientation change amount around the master roll axis Xm of the operation unit 101 is Xm(t+1)−Xm(t).

Here, consider a case where an operation of rolling the hand (fingers) of the slave arm 301 is performed. For example, in an endoscopic operation, a needle inserting operation is required for suturing. In such a suturing operation, a needle is inserted to a necessary part of the patient 20 while rolling the gripper serving as the end effector 303 attached to the hand (fingers) of the slave arm 301.

As described above, the slave arm 301 controls the position and orientation of the distal end effector while operating the seven joints 31, 32, 33, 34, 35, 36, and 37 in a coordinated manner. At this time, when Roll 1, which is a joint far from the end effector 303, is made to roll, and while the end effector 303 is also made to roll, the other joints 31, 32, 33, 35, 36, and 37 are also operated by a large amount, and consequently the joints 31, 32, 33, 35, 36, and 37 of the slave arm 301 may collide with surrounding organs and the like.

For this reason, when a rolling operation is mainly required, such as a suturing operation, it is desirable to roll Roll 2, which is a joint closer to the hand (fingers) of the slave arm 301, by a large amount and roll Roll 1, which is a joint far from the hand (fingers), by a small amount in order to prevent the other joints 31, 32, 33, 35, 36, and 37 from operating unnecessarily.

On the other hand, because the range of possible positions and orientations of the hand (fingers) of the slave arm 301 is greatly restricted if the movement of Roll 1 is restricted, in the case of an operation that requires rotation other than rolling, it is desirable to roll Roll 1 by a large amount. In this case, there is no particular problem even if Roll 2 is rolled by a small amount.

As to whether or not a command to mainly operate the roll axis joint at the distal end is issued by the operation of the operation unit 101, in a case where the position change amount by the operation of the operation unit 101 is equal to or less than a first threshold value and where the component of the orientation change amount about the master roll axis Xm is equal to or greater than a second threshold value, it can be determined that the position of the operation unit 101 has not changed so much and that the orientation has markedly changed around the master roll axis Xm. Therefore, in this case, the drive ratio α of the joint 31 on the distal end side of the two joints 31 and 34 in the redundant relationship is determined to be higher than that of the joint 34 on the base end side.

A method for controlling the slave arm 301 in accordance with the above concept will be described below with reference to the flowchart in FIG. 6.

Figure 6:
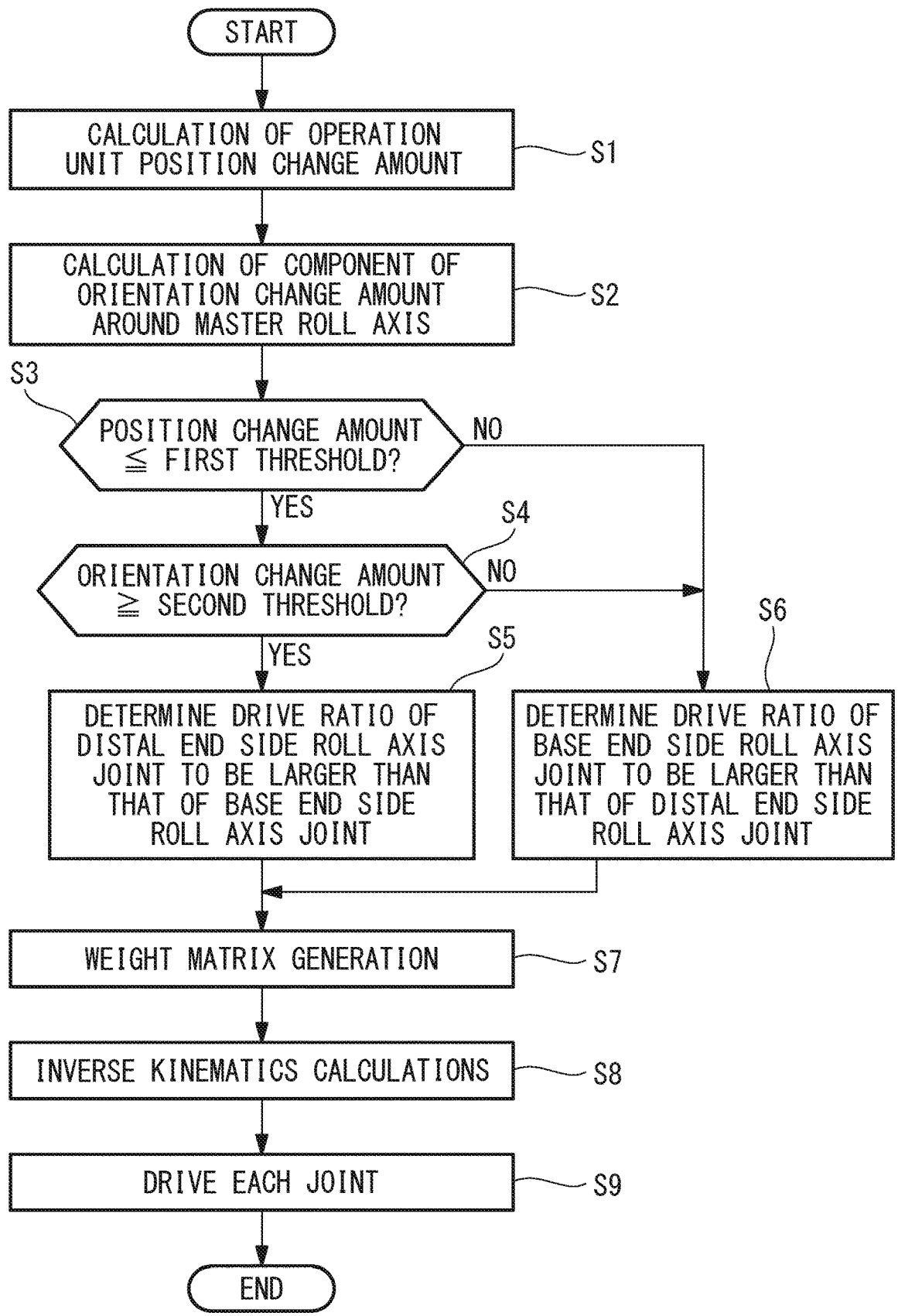
FIG. 6 is a flowchart for explaining the operation of the master-slave manipulator in FIG. 1.

The process in FIG. 6 is executed every predetermined time Δt.

In the process in FIG. 6, when operation signals are input from the remote operation device 100, the master controller 201 calculates a position change amount of the operation unit 101 from time t to time t+1 from the input operation signals (Step S1), and calculates an orientation change amount component around the master roll axis Xm (Step S2).

Then, it is determined whether or not the position change amount of the operation unit 101 calculated in step S1 is equal to or less than the first threshold value (step S3), and in the case where the position change amount of the operation unit 101 calculated in step S1 is equal to or less than the first threshold value, it is determined whether or not the orientation change amount component around the master roll axis Xm is greater than or equal to a second threshold value (step S4). When the orientation change amount component is equal to or greater than the second threshold value, the master controller 201 determines the drive ratio α of the joint 31 (Roll 2) to which the end effector 303 is attached to be larger than that of the joint 34 (Roll 1) in a redundant relationship with the joint 31 (step S5). In other cases, the drive ratio α of the base end joint 34 (Roll 1) away from the end effector 303 is determined to be larger than that of the joint (Roll 2) 31 in a redundant relationship with the joint 34 (step S6).

After the drive ratios α have been determined, the master controller 201 transmits the drive ratios α of the two redundant joints 31 and 34 together with the command values for commanding the position and orientation of the hand (fingers) of the slave arm 301 to the manipulator controller 202. In response to this, the manipulator controller 202 generates a weight matrix based on the drive ratios α (step S7), performs inverse kinematics calculations using the generated weight matrix (step S8), and calculates the drive amount of each of the joints 31, 32, 33, 34, 35, 36, and 37 of the slave arm 301.

Then, the manipulator controller 202 drives each of the joints 31, 32, 33, 34, 35, 36, and 37 of the slave arm 301 in accordance with the calculated drive amounts (step S9). For the inverse kinematics calculations, various conventionally known methods such as analytical methods can be used. Here, a detailed description of the inverse kinematics calculations is omitted.

As described above, according to the present embodiment, in the slave arm 301 having the joint Roll 2 for rolling the end effector 303 serving as the redundant joint 31 in addition to the joint Roll 1 for rolling the slave arm 301 itself, on the basis of the position change amount and orientation change amount of the operation unit 101 of the remote operation device 100, it is determined whether or not a command for an operation that mainly requires rolling, such as a suturing operation, has been issued.

Then, as a result of this determination, if it can be determined that an action that requires mainly rolling has been commanded, the drive ratio α of Roll 2 is determined to be larger than that of Roll 1 to generate a weight matrix, and the inverse kinematic calculations are performed using the generated weight matrix. On the other hand, if it can be determined that an action that requires movement for an orientation change other than rolling has been commanded, the drive ratio α of Roll 1 is determined to be larger than that of Roll 2 to generate a weight matrix, and the inverse kinematic calculations are performed using the generated weight matrix.

Thus, according to the present embodiment, in accordance with the position change amount and orientation change amount of the operation unit 101 every predetermined time, by changing the drive ratios α of Roll 1 and Roll 2, redundant degrees of freedom are selectively controlled while reflecting the intention of the operation of the operator 10, and intuitive operation including redundant degrees of freedom can be performed. In the present embodiment, the drive ratios α of Roll 1 and Roll 2 can be automatically determined, and it is not necessary to switch the drive joint with a switch or the like, and the labor of the operator 10 can be reduced.

In the example above, an example where the degrees of freedom of the operation unit 101 of the remote operation device 100 are 6 degrees of freedom (position 3 degrees of freedom, orientation 3 degrees of freedom), and the degrees of freedom of the slave arm 301 are 7 degrees of freedom (position 3 degrees of freedom, orientation 3 degrees of freedom, hand (fingers) rolling) is illustrated. On the other hand, the number of redundant joints 31 is not limited to one. For example, in FIG. 4, the technique of this embodiment can be applied even if another roll axis joint is disposed between the joint 32 and the joint 33.

Figure 7:
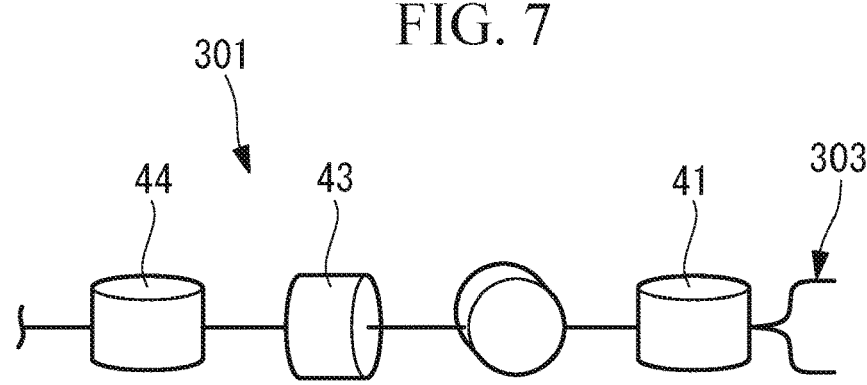
FIG. 7 is a diagram illustrating a first modification in which a redundant joint of the master-slave manipulator in FIG. 1 is a yaw axis joint.
Figure 8:
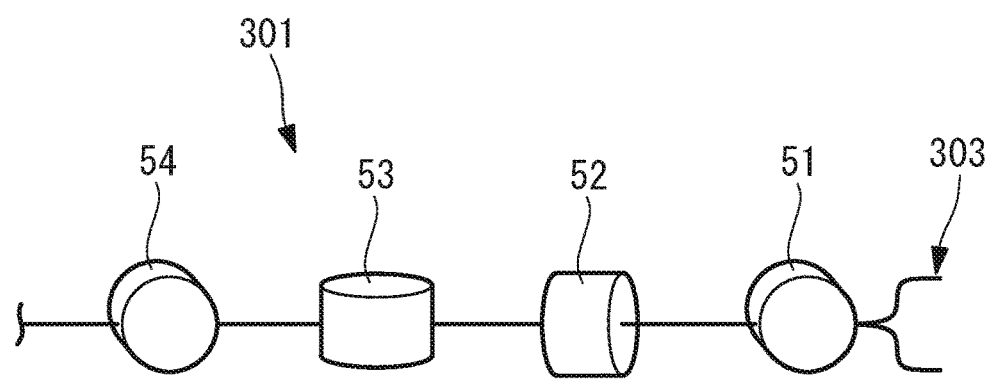
FIG. 8 is a diagram illustrating a second modification in which a redundant joint of the master-slave manipulator in FIG. 1 is a pitch axis joint.

In the example in FIG. 4, the redundant joint 31 to which the end effector 303 is attached is a roll axis joint; however, for example, as illustrated in FIG. 7, the above-described technique of the present embodiment can be applied even if the end effector 303 is attached to a yaw axis joint 41, and, as illustrated in FIG. 8, even if the end effector 303 is attached to a pitch axis joint 51.

In the case of the structure in FIG. 7, in the determination of step S4, the drive ratios α of the joints 41 and 44 in a redundant relationship are determined based on the orientation change component around the master yaw axis Zm. In the case of the structure in FIG. 8, in the determination in step S4, the drive ratios α of the joints 51 and 54 that drive in a redundant relationship may be determined based on the orientation change component around the master pitch axis Ym.

Thus, in this embodiment, the drive ratios α of the joints 41, 44, 51, and 54 in a redundant relationship are determined based on the position change amount and orientation change amount of the operation unit 101 of the remote operation device 100, so that it is possible to cope with the slave arm 301 of various structures.

In the example in FIG. 8, when the joint 52 is rotated 90 degrees, the joint 51 is equivalent to a yaw axis joint. In such a case, the determinations in steps S3 and S4 can be performed between the joint 51 and the joint 53. As described above, the determinations in steps S3 and S4 are not only performed using a relationship between the joints 51 and 54 whose rotation axes are parallel in the initial state, but can be performed using a relationship between the joints 51, 53, and 54 in which the rotation axes are parallel during driving in a redundant-degrees-of-freedom mechanism.

Figure 9:
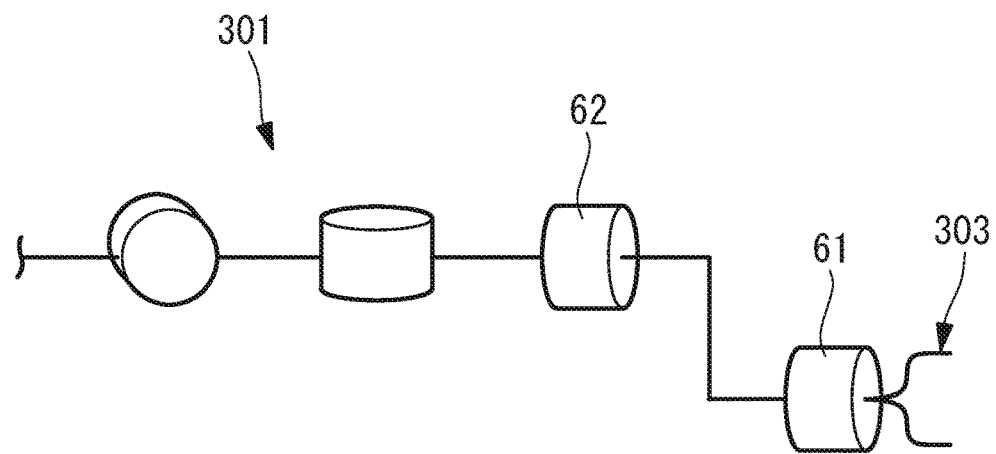
FIG. 9 is a diagram illustrating a configuration example of a slave arm in which, in the master-slave manipulator in FIG. 1, joints in a redundant relationship are adjacent and can be driven independently.

In each of the examples described above, between the joints 31, 34, 41, 44, 51, and 54 having parallel rotation axes and a redundant relationship, the slave arm 301 having a structure in which the joints 33, 43, and 53 having an independent relationship in which the rotation axis is orthogonal to the joint are illustrated. In actuality, if each of the joints 31, 32, 33, 34, 35, 36, 37, 41, 43, 44, 51, 52, 53, and 54 constituting the slave arm 301 is driven independently, the joints 31, 34, 41, 44, 51, and 54 in a redundant relationship may be disposed adjacent to each other. For example, the technique of the present embodiment described above can be applied to a joint 61 and a joint 62 even in a structure like that illustrated in FIG. 9.

In the present embodiment, among the joints 31 and 34 in a redundant relationship, as a condition for determining the drive ratio α of the joint 31 disposed on the distal end side to be higher than that of the joint 34 disposed on the base end side, a case where the position change amount of the operation unit 101 is equal to or less than the first threshold value and the orientation change amount around the predetermined axis is equal to or greater than the second threshold value is exemplified. However, instead of this, the condition may be a case where the gripper serving as the end effector 303 can be determined as holding the suture needle or suture.

As the case where the gripper (end effector) 303 can be determined as holding the suture needle or suture, the case where an operation command for closing the gripper 303 by gripping the gripper unit 106 is input, and the drive voltage of (drive input to) the gripper 303 is equal to or higher than a predetermined threshold (third threshold) can be taken as an example. When the operator 10 intends to close the gripper 303 and the gripper 303 is maintained without being completely closed, it can be determined that the gripper 303 is holding a suture needle or suture.

Alternatively, it may be determined that the suture needle or suture is grasped by processing an endoscopic image of the gripper 303. This also makes it possible to directly determine whether the suture needle or suture is grasped.

In this embodiment, in a case where the roll axis is redundant, the drive ratios α of the joints 31 and 34 in a redundant relationship were calculated using the magnitude of the orientation change component around the master roll axis Xm; however, instead, even in a case where the roll axis is redundant, if the orientation change amount component around any axis of the operation unit 101 is large, it may be determined that the hand (fingers) is being operated, and the drive ratio α of the joint closer to the end effector 303 may be made larger than that of the joint on the far side.

In this case, the determination may be made using the roll axis, the pitch axis, and the yaw axis individually, or may be determined using an orientation change amount assuming a single rotation axis.

In the present embodiment, the drive ratios α of the joints 31 and 34 in a redundant relationship are calculated on the basis of the position change amount and the orientation change amount of the operation unit 101; however, instead, in the case where the total bending angle of the joints 32, 33, 35, 36, and 37 other than the redundant joints 31 and 34 is equal to or greater than a predetermined threshold, the drive ratio α of the joint closer to the end effector 303 may be made larger than that of the joint on the far side.

In this case, since the slave arm 301 has a configuration in which each of the joints 31, 32, 33, 34, 35, 36, and 37 is bent so as to be folded, and is in a form that interferes with surrounding tissues and the like, it can be estimated that a sewing operation is being performed. Therefore, by making the drive ratio α of the joint closer to the end effector 303 larger than that of the joint on the far side, work can be performed without causing interference with the surroundings.

Figure 10:
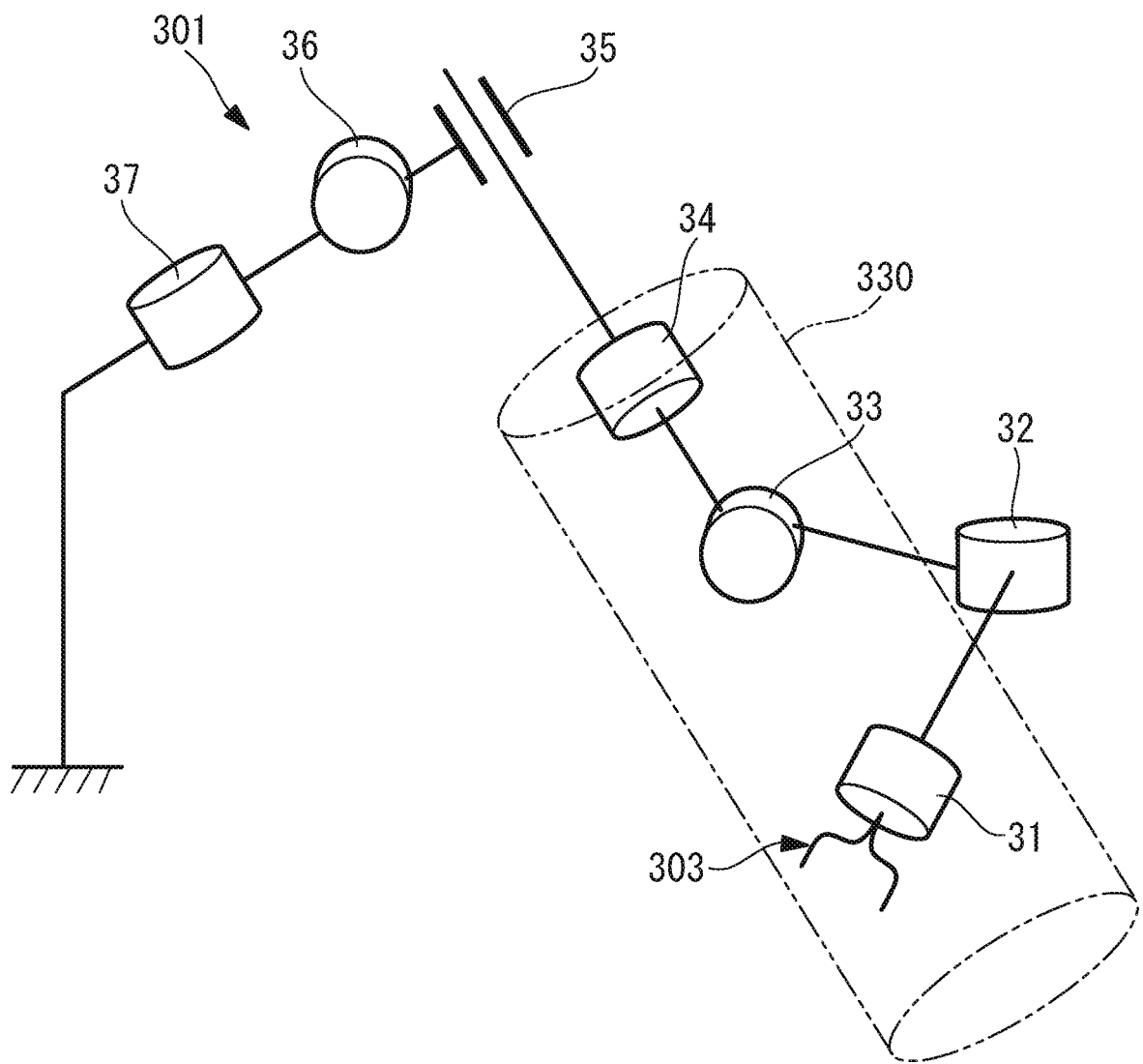
FIG. 10 is a diagram illustrating another modification for determining whether or not work is being performed by the slave manipulator of the master-slave manipulator of FIG. 1.

As illustrated in FIG. 10, assuming a virtual cylinder 330 extending along the advance-retract axis of the slave arm 301, when the slave arm 301 comes in contact with the virtual cylinder 330, among the joints 31 and 34 in a redundant relationship, the drive ratio α of the joint on the distal end side may be determined to be higher than that on the base end side.

The operator 10 may switch the drive ratios α of a plurality of joints in a redundant relationship with a switch, a foot switch, a voice switch, or the like provided in the operation unit 101 of the remote operation device 100.

Figure 11:
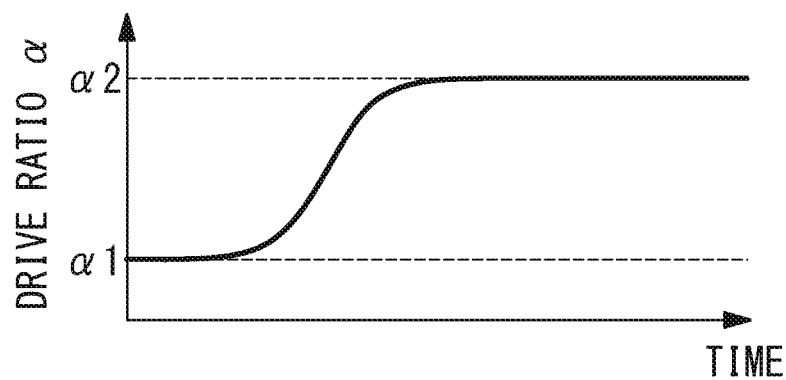
FIG. 11 is a diagram illustrating an example in which the drive ratios are continuously changed.
Figure 12:
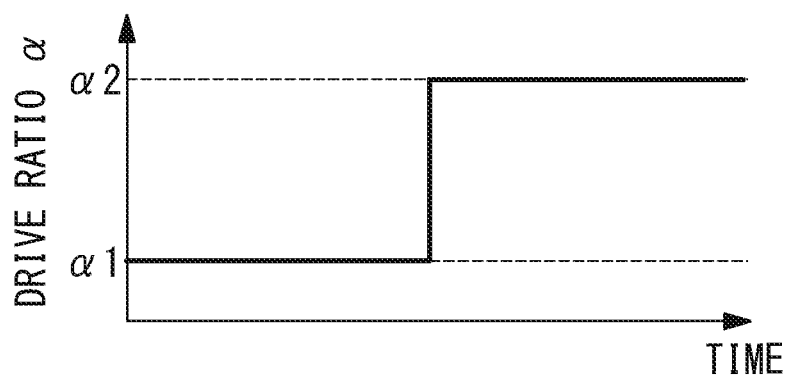
FIG. 12 is a diagram illustrating an example in which the drive ratios are changed in a stepwise manner.

When the master controller 201 switches the drive ratios α, the drive ratios may be continuously changed between two drive ratios α1 and α2, as illustrated in FIG. 11, or may be changed in a stepwise manner, as illustrated in FIG. 12. In the case of a continuous change, for example, the drive ratios α may be changed according to a quadratic function or a sigmoid function, or may be dulled by a low-pass filter or the like.

In the case where the drive ratios α are continuously changed, the drive ratio α of the joint on the distal end side close to the end effector 303 increases as the rotation speed of the operation unit 101 increases, that is, the drive ratio α may be determined by a function that is positively correlated with the rotation speed, and the drive ratio α of the joint on the base side far from the end effector 303 increases as the translation speed of the operation unit 101 increases, that is, the drive ratio α may be determined by a function that is positively correlated with the translation speed.

Since translational movement is mainly performed when the slave arm 301 is moved by a large amount, and rotational movement is mainly performed when the hand (fingers) of the slave arm 301 is moved by a small amount, the drive ratios α can be appropriately determined by the above functions. Instead of the functions, the drive ratios α may be determined by using a table.

The drive ratios α of the joints in a redundant relationship may be visually presented to the operator 10 by being displayed on the display unit 102. As a display method, any display method such as display using numbers, display using various graphs, display using a schematic diagram, or display in which a color chart is superimposed on an endoscope screen can be employed.

Although the present invention has been described based on the above embodiments, the present invention is not limited to the above embodiments, and changes and modifications may be optionally made without departing from the scope of the present invention.

Furthermore, the above-described embodiments include inventions at various stages, and various inventions can be derived by appropriately combining a plurality of disclosed constituent elements. For example, even if some constituent elements are eliminated from all the constituent elements illustrated in the embodiment, so long as the above-described problems can be solved and the above-described effects can be obtained, a configuration from which these constituent elements are eliminated can also be derived as an invention.

As a result, the following aspects are derived from the above embodiment.

According to an aspect of the present invention, a master-slave manipulator includes a remote operation device, serving as a master, that provides operation information corresponding to multiple degrees of freedom, a slave manipulator having a plurality of joints corresponding to multiple degrees of freedom, and including redundant joints among the joints, and a controller that controls the operation of the joints in accordance with the operation information, and the controller, depending on whether or not work is being performed by the slave manipulator, determines the drive ratios α (0<α<1) of the joints in a redundant relationship and drives these joints.

According to this aspect, when the operator operates the remote operation device and inputs operation information corresponding to multiple degrees of freedom, the plurality of joints corresponding to the plurality of degrees of freedom of the slave manipulator are operated. In this case, when operation information including the degrees of freedom of the redundant joints provided in the slave manipulator is input, the controller, depending on whether or not work is being performed by the slave manipulator, determines drive ratios α (0<α<1) of the joints in a redundant relationship and simultaneously drives two or more of the joints in a redundant relationship. Thereby, even if the remote operation device and the slave arm have different structures, it is possible to selectively control the redundant degrees of freedom and perform an intuitive operation including the redundant degrees of freedom.

In the above aspect, the controller may calculate a position change amount and an orientation change amount of the remote operation device from the operation information, and may determine the drive ratios α (0<α<1) of the joints in a redundant relationship using the calculated position change amount and orientation change amount, and drive the joints.

By doing this, the position change amount and orientation change amount of the remote operation device are calculated by the controller from the input operation information, drive ratios are determined using the calculated position change amount and orientation change amount, and two or more of the joints in a redundant relationship are driven simultaneously.

In the above aspect, the controller has a position change amount equal to or less than a first threshold value, and in the case where a component around a specified axis of the orientation change amount is equal to or greater than a second threshold value, among the joints in a redundant relationship, the drive ratio of the joint arranged on the distal end side may be determined to be higher than that of the joint arranged on the base end side.

By doing this, in the case where the position of the remote operation device does not move much and the orientation moves by a large amount around a specified axis, it is presumed that operation of the end effector provided at the distal end of the slave manipulator is mainly commanded. Accordingly, among the joints that are in a redundant relationship, the drive ratio of the joint on the distal end side is set to be higher than that of the joint on the base end side so that the distal end of the slave manipulator can be moved by a large amount while suppressing movement of the entire slave manipulator. Thereby, the slave manipulator can be operated while reducing interference with the surroundings.

In the above aspect, the specified axis may be the axis of the remote operation device corresponding to the longitudinal axis of the end effector provided at the distal end of the slave manipulator.

By doing so, the end effector at the distal end of the slave manipulator can be rotated around the longitudinal axis while reducing interference with the surroundings.

In the above aspect, the specified axis may be a rotation axis before and after the orientation change of the remote operation device.

By doing this, regardless of the direction of change in the orientation of the remote operation device, if the orientation change amount is large, because it is presumed that the operation of the end effector provided at the distal end of the slave manipulator is mainly commanded, among the joints that have a redundant relationship, the drive ratio of the joint on the distal end side is set to be higher than that of the joint on the base end side, and the distal end of the slave manipulator can be moved by a large amount while suppressing the movement of the entire slave manipulator.

In the above aspect, the end effector provided at the distal end of the slave manipulator is a gripper, and, in the case where it is determined that the gripper is holding a suture needle or suture, the controller may determine, among the joints in a redundant relationship, the drive ratio of the joint on the distal end side to be higher than that on the base end side.

In this way, when it is determined that the gripper is holding the suture needle or suture, it can be estimated that a sewing operation using the suture needle or suture is being performed. Therefore, in such a case, among the joints in a redundant relationship, the drive ratio of the joint on the distal end side is set to be higher than that on the base end side, the movement of the entire slave manipulator is suppressed, and the gripper can be operated by a large amount so as to easily perform the suturing operation.

In the above aspect, the controller may determine that the suture needle or the suture is grasped when the gripper is in a closed state and a drive input to the gripper is equal to or greater than a third threshold value.

In this way, when the gripper is commanded to be in the closed state and the drive input to the gripper is large, it can be estimated that the sewing operation is performed while the suture needle or the suture is held.

In the above aspect, the controller may determine that the suture needle or the suture is held based on an endoscopic image obtained by capturing an image of the gripper.

In this way, it can be directly determined that the gripper illustrated in the endoscopic image is holding the suture needle or suture.

In the above aspect, the controller, when the total angle of the joints other than the redundant joints of the slave manipulator is equal to or greater than a predetermined threshold value, among the joints in a redundant relationship, may determine the drive ratio of the joint on the distal end side to be higher than that on the base end side.

By doing this, in the case where the total angle of joints other than the redundant joints is equal to or greater than a predetermined threshold, it can be estimated that the slave manipulator has an orientation in which each joint is greatly bent and is an orientation for performing work such as suturing work. Therefore, by determining the drive ratio of the distal end joint to be higher than that of the base end joint, the distal end of the slave manipulator can be moved greatly while suppressing movement of the entire slave manipulator.

In the above aspect, in the case where the slave manipulator contacts a virtual cylinder having a predetermined radius along the advance-retract axis of the slave manipulator, the controller may determine, among the joints in a redundant relationship, the drive ratio of the joint on the distal end side to be higher than that on the base end side.

By doing this, the slave manipulator can be easily estimated that each joint is in a working state, and in the case of being in a working state, the distal end of the slave manipulator can be moved by a large amount while suppressing the movement of the entire slave manipulator.

In the above aspect, an input unit that is operated by an operator is provided, and the controller may determine the drive ratios of the two or more joints that are in a redundant relationship in accordance with an input from the operator to the input unit.

By doing so, it is possible to perform an appropriate operation with the slave manipulator by switching the drive ratios according to the judgment of the operator.

In the above aspect, when the controller changes the drive ratios, the drive ratios may be changed continuously.

In this way, the operating state of the slave manipulator can be shifted by smoothly changing the drive ratios between a state in which the joint on the distal end side is moved by a large amount and a state in which the joint on the base end side is moved by a large amount.

In the above aspect, the remote operation device can input a translation operation and a rotation operation by an operator, the controller may determine the drive ratio of the joint on the base end side among the joints in a redundant relationship by using a function positively correlated with the translation speed of the remote operation device, and may determine the drive ratio of the joint on the distal end side by using a function positively correlated with the rotational speed of the remote operation device.

In this way, when the operator translates the remote operation device by a large amount, the drive ratio of the joint on the base end side can be increased and the entire slave manipulator can be moved by a large amount, and when the operator markedly changes the orientation of the remote operation device, the drive ratio of the joint on the distal end side can be increased and the distal end side of the slave manipulator can be moved by a large amount.

In the above aspect, when the controller changes the drive ratios, the drive ratios may be changed in a step-wise manner.

In this way, among the joints in a redundant relationship, the operating state of the slave manipulator can be quickly changed between the state in which the joint on the distal end side is moved by a large amount and the state in which the joint on the base end side is moved by a large amount.

In the above aspect, a display unit which displays the drive ratios may be provided.

In this way, the operating state of the slave manipulator can be checked at a glance by checking the drive ratios displayed on the display unit.

In another aspect of the present invention, a method for controlling a master-slave manipulator that includes a slave manipulator having a plurality of joins corresponding to multiple degrees of freedom and including redundant joints among the joints, includes calculating a position change amount and an orientation change amount of a remote operation device from operation information corresponding to multiple degrees of freedom obtained from the remote operation device, serving as a master, using the calculated position change amount and the orientation change amount to determine drive ratios α (0<α<1) of the joints in a redundant relationship, and controlling movement of the joints according to the obtained operation information and the determined drive ratios.

REFERENCE SIGNS LIST 1 master-slave manipulator
10 operator
31, 34, 41, 44, 51, 54 joints (redundant joints)
32, 33, 35, 36, 37, 52, 53 joints
100 remote operation device
101 operation unit (input unit)
102 display unit
200 controller (control device)
300 slave manipulator
303 gripper (end effector)
330 virtual cylinder
α drive ratio

The invention claimed is:

1. A master-slave manipulator comprising:
a remote operation device, serving as a master, that is configured to provide operation information corresponding to multiple degrees of freedom;
a slave manipulator having a plurality of joints corresponding to multiple degrees of freedom and including a redundant joints among the joints; and
a controller that is configured to control the operation of the joints in accordance with the operation information,
wherein, when it is determined that a distal end of the slave manipulator operates, the controller determines, among the joints in a redundant relationship, drive ratios α of a joint disposed on a base end side to a joint disposed on a distal end side within a range of 0<α<1, respectively, and drives these joints.

2. The master-slave manipulator according to claim 1, wherein, when the position change amount of the remote operation device calculated by the controller from the operation information is equal to or less than a first threshold value, and a component of the orientation change amount around a predetermined axis calculated from the operation information is equal to or greater than a second threshold value, the controller determines that the distal end of the slave manipulator operates.

3. The master-slave manipulator according to claim 2, wherein the predetermined axis is an axis of the remote operation device corresponding to a longitudinal axis of an end effector provided at a distal end of the slave manipulator.

4. The master-slave manipulator according to claim 2, wherein the predetermined axis is a rotation axis from before the orientation change to after the orientation change of the remote operation device.

5. The master-slave manipulator according to claim 1, wherein the controller determines whether the distal end of the slave manipulator operates when a sum of angles of the joints other than the redundant joints of the slave manipulator is equal to or greater than a predetermined threshold.

6. The master-slave manipulator according to claim 1, wherein the controller determines whether the distal end of the slave manipulator operates when the slave manipulator contacts a virtual cylinder having a predetermined radius along an advance-retract axis of the slave manipulator.

7. The master-slave manipulator according to claim 1, wherein the controller continuously changes the drive ratios.

8. The master-slave manipulator according to claim 7, wherein it is possible that the remote operation device inputs a translation operation and a rotation operation from an operator,
the controller determines the drive ratio of the joint on the base end side among the joints in a redundant relationship by a function positively correlated with a translation speed of the remote operation device, and determines the drive ratio of the joint on the distal end side according to a function positively correlated with a rotational speed of the remote operation device.

9. The master-slave manipulator according to claim 1, wherein the controller changes the drive ratios in a stepwise manner.

10. The master slave manipulator according to claim 1, further comprising:
a display unit that is configured to display the drive ratios.

11. A master-slave manipulator comprising:
a remote operation device serving as a master that is configured to provide operation information corresponding to multiple degrees of freedom;
a slave manipulator having a plurality of joints corresponding to multiple degrees of freedom and including a redundant joints among the joints;
a controller that is configured to control operation of the joints according to the operation information; and
an end effector provided at a distal end of the slave manipulator,
wherein the end effector is a gripper, and
when it is determined that the gripper is holding a suture needle or suture, the controller determines, depending on whether or not work is being performed by the slave manipulator, among the joints in a redundant relationship, drive ratios α (0<α<1) or drive amounts of a joint arranged on a base end side to a joint arranged on the distal end side, respectively, and drives these joints.

12. The master-slave manipulator according to claim 11, wherein the controller determines that the suture needle or the suture is grasped when the gripper is in a closed state and a drive input to the gripper is a third threshold value or more.

13. The master-slave manipulator according to claim 11, wherein the controller determines that the suture needle or the suture is grasped based on an endoscopic image obtained by capturing an image of the gripper.

14. A master-slave manipulator comprising:
a remote operation device, serving as a master, that is configured to provide operation information corresponding to multiple degrees of freedom;
a slave manipulator having a plurality of joints corresponding to multiple degrees of freedom and including a redundant joints among the joints;
a controller that is configured to control the operation of the joints according to the operation information; and
an input unit operated by the operator,
wherein the controller determines whether or not work is being performed by the slave manipulator according to an input by the operator to the input unit, and determines drive ratios α (0<α<1) or drive amounts of two or more of the joints in a redundant relationship and drives these joints.

* * * * *